(12) United States Patent
Dubach

(10) Patent No.: US 8,491,592 B2
(45) Date of Patent: Jul. 23, 2013

(54) DEVICE FOR THE APPLICATION OF BONE SUBSTITUTE MATERIAL

(75) Inventor: Werner F. Dubach, Maur (CH)

(73) Assignee: Geistlich Pharma AG, Wolhusen (CH)

( * ) Notice: Subject to any disclaimer, the term of this patent is extended or adjusted under 35 U.S.C. 154(b) by 139 days.

(21) Appl. No.: 13/250,383

(22) Filed: Sep. 30, 2011

(65) Prior Publication Data

US 2012/0083790 A1    Apr. 5, 2012

(30) Foreign Application Priority Data

Oct. 1, 2010   (EP) .................................... 10185348

(51) Int. Cl.
*A61B 17/58* (2006.01)
*A61B 17/60* (2006.01)
*A61F 2/00* (2006.01)

(52) U.S. Cl.
USPC .............................. 606/93; 606/92; 606/94

(58) Field of Classification Search
USPC .............. 606/92–94; 604/82, 89–91
See application file for complete search history.

(56) References Cited

U.S. PATENT DOCUMENTS

| 4,060,082 | A  | 11/1977 | Lindberg et al. |
| 6,319,002 | B1 | 11/2001 | Pond |
| 7,118,378 | B1 | 10/2006 | Karapetyan |
| 2003/0069545 | A1 | 4/2003 | Arm |

FOREIGN PATENT DOCUMENTS

| WO | WO 99/20330 A1 | 4/1999 |
| WO | WO 2006/125100 A1 | 11/2006 |
| WO | WO 2008/022481 A1 | 2/2008 |
| WO | WO 2008/153513 A2 | 12/2008 |

OTHER PUBLICATIONS

Extended European Search Report and Written Opinion of the European Patent Office for European patent application No. 11 18 3473, dated Feb. 7, 2012 (6 pages).
Extended European Search Report and Opinion of the European Patent Ofice for European patent application No. 10 185 348.9, dated Jul. 28, 2011 (9 pages).

*Primary Examiner* — Andrew Yang
(74) *Attorney, Agent, or Firm* — Wolf, Greenfield & Sacks, P.C.

(57) ABSTRACT

An application device for bone substitute material is disclosed. A cylinder contains a piston rod having an elastically deformable piston. The cylinder is closed via an attachment, through which a wetting liquid phase can be inserted via an injection opening. After a period of time, the wetted bone substitute material is compressed, with excess liquid phase being pressed out through drainage openings. Thereafter, the attachment can be removed and if applicable discharging takes place through a curved discharge nozzle, with the piston being able to adapt itself to the curvature with the benefit of total emptying of the device.

12 Claims, 5 Drawing Sheets

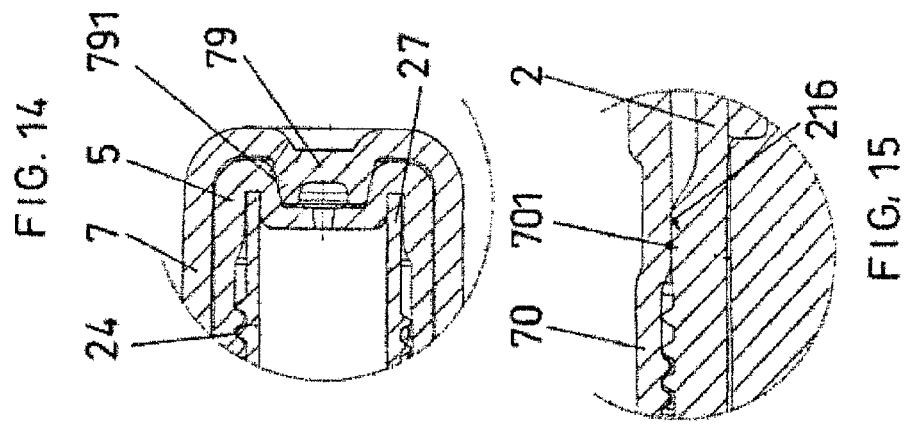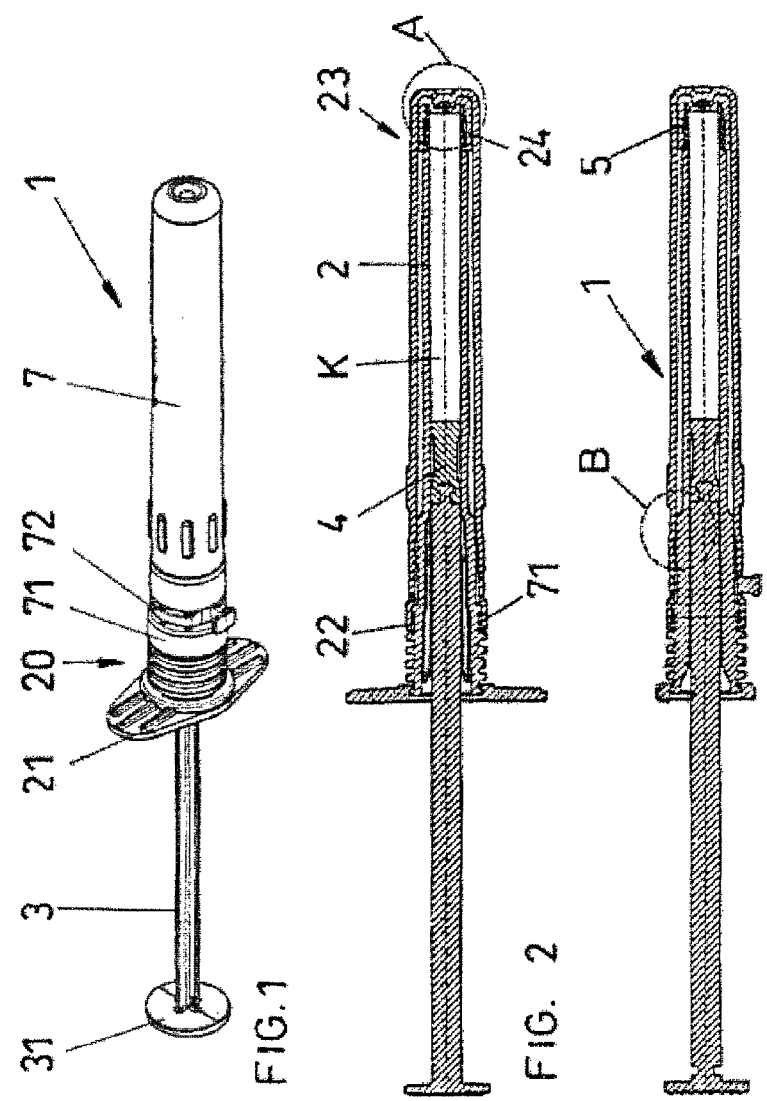

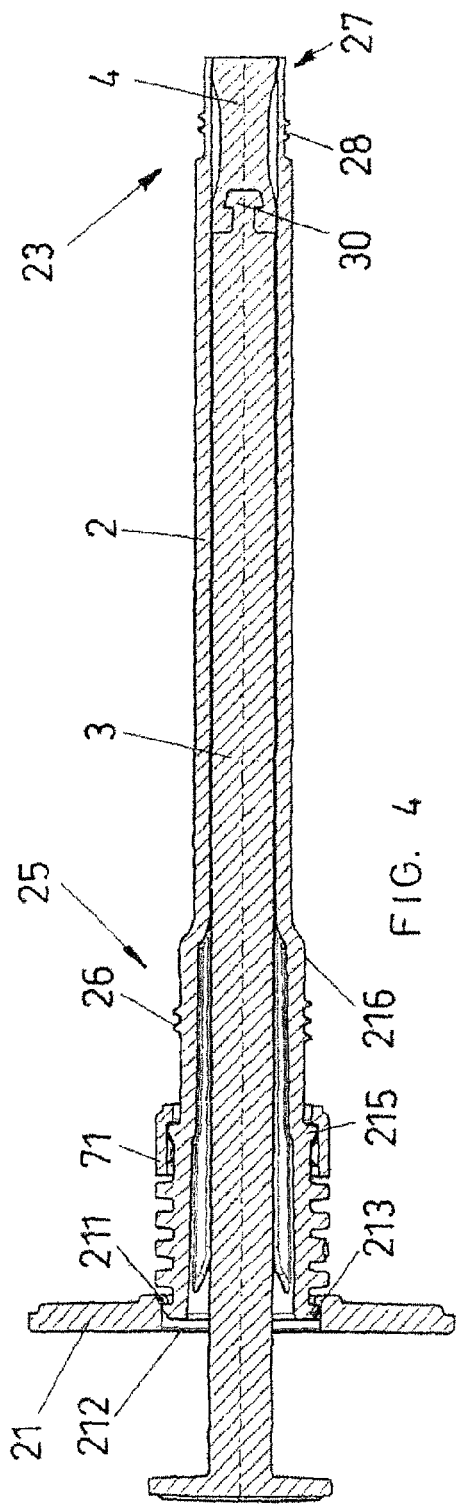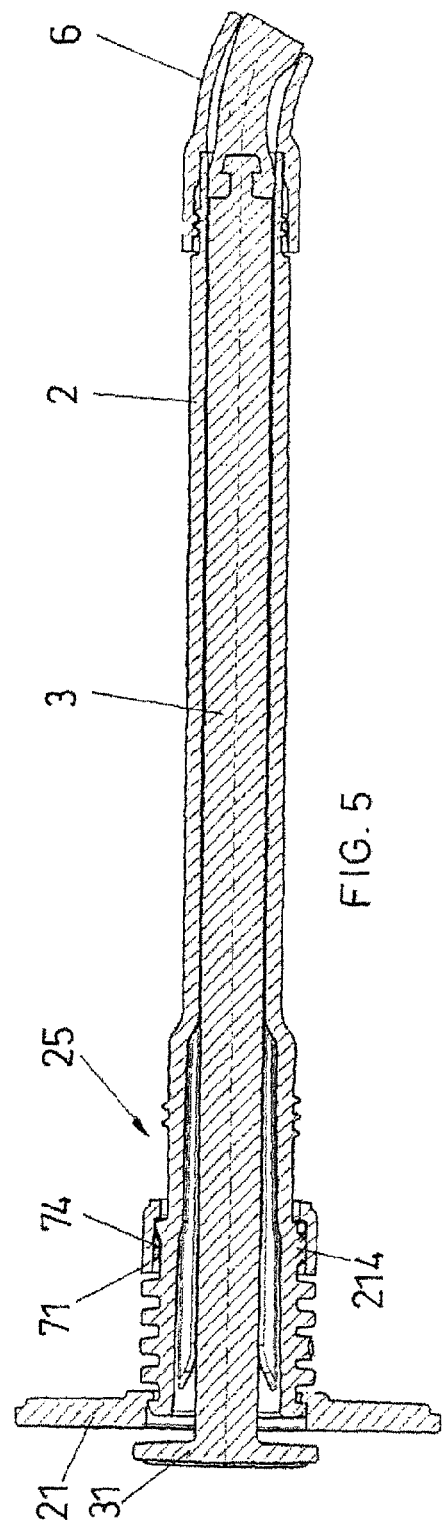

FIG. 6
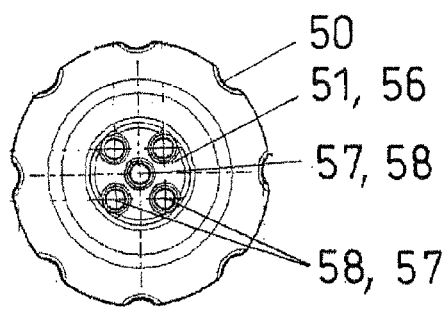
FIG. 7
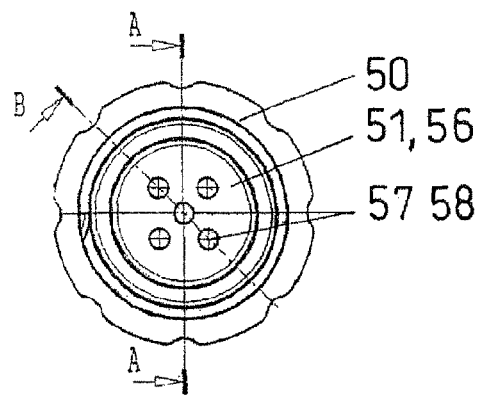
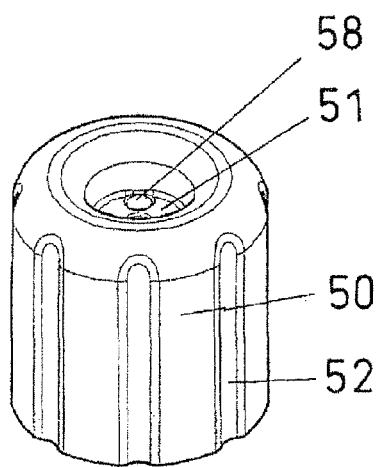
FIG. 8
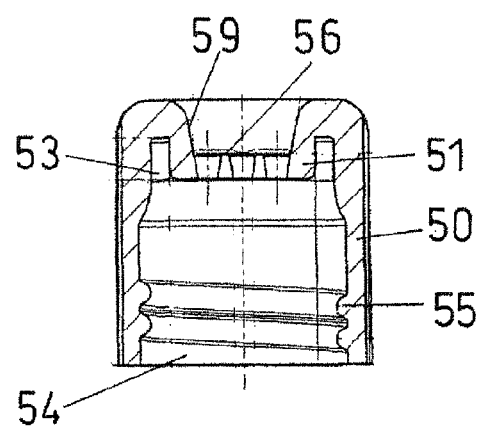
FIG. 9
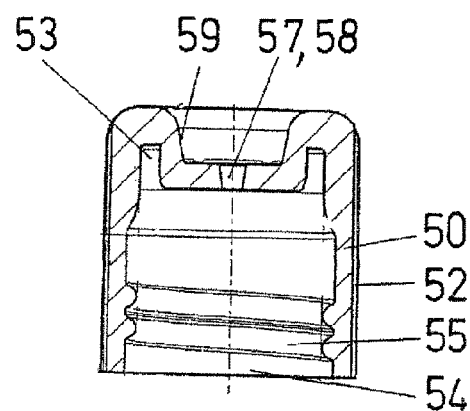
FIG. 10

US 8,491,592 B2

DEVICE FOR THE APPLICATION OF BONE SUBSTITUTE MATERIAL

CROSS REFERENCE TO RELATED APPLICATIONS

Foreign priority benefits are claimed under 35 U.S.C. §119(a)-(d) or 35 U.S.C. §365(b) to European Patent Application No. 10 185 348.9, filed Oct. 1, 2010, which is hereby incorporated by reference in its entirety.

BACKGROUND

1. Field

Aspects relate to a device for the application of bone substitute material especially for use in the dental, orthopedic or esthetic field, comprising a cylinder.

2. Discussion of Related Art

In dentistry, bone substitute material is used, in part, in order to fill larger cavities after extractions or resections. Thus, an interpenetration of the cavity with soft tissue is prevented and the build-up of bone is accelerated, because bone is necessary to form a stable base for teeth, implants and prostheses. This bone substitute material is extremely costly and, accordingly, one aim of the present disclosure is to minimize material loss during application.

The granulate bone substitute material is designed to be mixed with a liquid phase. That liquid phase may be e.g. the patient's own blood or a physiological saline solution. The granulate bone substitute material may be any of the numerous materials and compositions of synthetic or natural origin that are known to stimulate bone formation, bone regeneration, bone repair, bone remodeling and/or bone replacement. An example of a suitable bone replacement of natural origin is Geistlich Bio-Oss®, commercially available from Geistlich Pharma AG, which is manufactured from natural bone by a process described in U.S. Pat. No. 5,167,961. An example of a suitable bone replacement of synthetic origin is a granulate of the biphasic calcium phosphate/hydroxyapatite material described in international application PCT/EP2010/003590.

Conventionally, the supplied granulate is prepared in a container and a liquid phase is added, after which the product, which is present in granulate form, is wetted. Care is to be taken here that the liquid phase is in a correct ratio, so that the wetted material has a pasty consistency. In the case where a certain excess of the liquid phase is present, the latter should be drained by means of a sieve. This handling is time-consuming, must be carried out carefully and accordingly this is done by the practitioner who is carrying out the treatment. Once the mixture is prepared, it must be drawn up by means of a syringe consisting of a cylinder and piston rod with a correspondingly sealing piston, or by using a surgical scoop to implant the product in the patient. If the material is relatively fluid, then it can indeed be taken up well, but when the prepared material has to be applied in the upper jaw, then the loss of material is relatively high. If, however, the material is more firm in consistency, then drawing the material into the syringe can be difficult even though material loss is minimized.

Devices have been known since the 1980s, in which the mineral component is stored in a cylinder of a first application syringe, and then by means of a second injection syringe, which is able to be coupled with the first, the collagen phase, i.e. the liquid phase, is added to the mineral component. For a corresponding thorough mixing, the two injection syringes, which are coupled with each other, can be moved so that the mixture is able to be moved from one syringe into the other syringe. For this solution to function at all, however, the entire mixture must be relatively fluid. Such a two-syringe device is described for example in EP-A-0266058.

As already mentioned, it may be beneficial when the material has a high viscosity, but the material then will tend clog when it pressed through a constriction. This problem has already been recognized and accordingly, for example, document US 2006/0264964 shows in FIG. 5 a solution in which the material is discharged via a discharge nozzle, wherein this discharge nozzle has the same internal diameter as the tube on which it is fastened. Reference is to be made in particular to FIGS. 5 and 7 in this respect. This publication clearly shows that by means of the piston cylinder unit the material can be pushed forward out from the cylinder only up to the discharge nozzle, the bone substitute material remaining in the discharge nozzle being therefore lost.

Document US-B-7118378 teaches another solution which is designed especially for dental applications and accordingly realizes the supply via a curved discharge nozzle. Here, the entire cylinder is embodied in a curved version. Accordingly, the piston rod must be elastically deformable. Such a solution is not without problems, notably because such cylinders cannot be manufactured by injection molding techniques, and therefore must be manufactured from a thermoplastic tube which is subsequently bent. This leads to practically uncontrollable alterations in the cross-section in the bending region. Accordingly, such a device tends to become jammed. Instead of a piston, two sealing rings are now pushed onto the thinned end of the piston rod, which are intended to undertake this function. As a mixing is to be carried out here in the cylinder and one is aware of the problem of the blocking of the material, the discharge nozzle itself has been embodied so as to be running in a straight line, and the material is only mixed in this region. Therefore, the piston per se is to be regarded as a rigid element and accordingly this piston does not act in the curvature region. However, this also means that the actual curvature scarcely comes to lie in the patient's mouth, but rather outside the pharynx. The desired advantage, namely of feeding the relatively highly viscous material directly in the region of the application in a curved path, hence cannot be achieved with this prior art device.

Document WO-A-2008/153513 discloses a syringe-type delivery device for the application of bone graft material comprising a cylinder, in which the ready-mixed bone substitute material is situated, with an end on the holding side and an end on the discharge side, wherein a piston rod is situated in the cylinder, on which piston rod a sealing piston is placed. A removable attachment with a straight or curved cannula for discharging the bone substitute material engages via a threaded adapter with an external thread on the discharge side end of the cylinder.

Similarly, document WO-A-2006/125100 discloses a graft syringe assembly for the provision of bone graft material to anatomical structures. The assembly has a syringe barrel including external threads on its distal end which are adapted for engaging the inner threads of a syringe adapter. In order to offer flexibility with the delivery point of bone graft material, a flexible delivery tube is attached to the syringe adapter by a luer fitting. In order to mix the bone graft material and other fluids in the device, fluid may be introduced by a needle or another device through an opening in the syringe adapter or through an alternative site port provided on the syringe barrel.

Document US-A-2003/0069545 shows also a similar graft delivery syringe which can mix and dispense solid bone substitute and fluid additives for the implantation of bone replacement materials. The syringe comprises a cylindrical syringe barrel and a piston connected to a rubber plunger. To introduce fluids into the inner cavity defined by the syringe barrel, the rubber plunger includes an X-shaped opening, which also allows air and excess fluid to escape from the barrel.

SUMMARY

However, the inventors have recognized that none of the above prior art documents discloses drainage openings provided on the adapter/attachment or elsewhere on the syringe, in particular several drainage openings arranged around the injection opening of a replaceable attachment. Thus, a mixture with a high viscosity may be reliably achieved. This material with a high viscosity is to be supplied to the patient as close as possible to the discharge site in a curved path, wherein at the same time it is to be ensured that the material can be discharged practically without loss.

In one embodiment, a device for the application of bone substitute material includes a cylinder, in which the bone substitute material is situated in granular consistency, with an end on the holding side and an end on the discharge side, and a piston rod situated in the cylinder. A sealing piston is placed on the sealing rod. The end of the cylinder on the discharge side is provided with an external thread, on which a removable attachment with an internal thread and adapted to close the cylinder is held. The device also includes a curved discharge nozzle which can replace the attachment and be held on the end of the cylinder on the discharge side provided with the external thread. The sealing piston is a single-piece, rubber-elastic and flexible element, the length of which corresponds at least approximately to the length of the curved discharge nozzle. The attachment is provided with an injection opening for injecting fluid into the cylinder where the granular bone substitute material is situated. Several drainage openings are arranged around the injection opening.

In another embodiment, a device for the application of bone substitute material is disclosed. The device includes a cylinder having a proximal end and a discharge end. The cylinder contains the bone substitute material in granular form. A removable attachment is held on the discharge end and is adapted to close the cylinder. The removable attachment include an injection opening for injecting fluid into the cylinder and several drainage openings arranged around the injection opening. A piston rod is disposed in the cylinder and a sealing piston is placed on the piston rod. In yet another embodiment, the bone substitute material has a consistency in the form of a rope, i.e. with high viscosity.

Various embodiments of the present invention provide certain advantages. Not all embodiments of the invention share the same advantages and those that do may not share them under all circumstances.

Further features and advantages of the present invention, as well as the structure of various embodiments of the present invention are described in detail below with reference to the accompanying drawings.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. Various embodiments of the invention will now be described, by way of example, with reference to the accompanying drawings, in which:

FIG. 1 shows the device according to one embodiment of the invention before the first use, in perspective view;

FIG. 2 is a central longitudinal section of the device shown in FIG. 1;

FIG. 3 shows the same view in FIG. 2, but rotated through 90°;

FIG. 4 is a central longitudinal section of the device shown after the removal of the closure sleeve and after the first use, without a discharge nozzle;

FIG. 5 illustrates the device with a discharge nozzle embodied in a curved shape, which enables a total emptying of the device;

FIG. 6 shows an attachment able to be placed onto the cylinder, with a view in the rotation axis from the exterior;

FIG. 7 shows the same attachment as FIG. 6 with a view onto the inner side;

FIG. 8 shows the attachment in perspective representation;

FIG. 9 shows a diametral vertical section through the attachment along the line B-B of FIG. 7;

FIG. 10 shows the attachment in a diametral longitudinal section rotated through 45° along the line A-A, as again illustrated in FIG. 7;

FIG. 14 shows a detail of the cooperating seal between the closure sleeve and the attachment in a device before the first use;

FIG. 15 shows in a section a detail with respect to the seal of the closure sleeve relative to the cylinder of the device;

DETAILED DESCRIPTION

Figure 11:
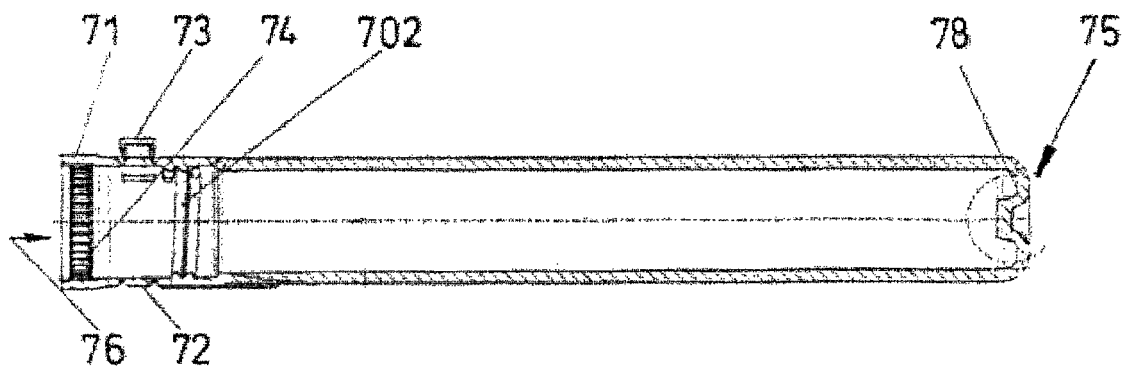
FIG. 11 shows a central longitudinal section through the closure sleeve on its own.

In FIGS. 1 to 3, the application device 1 according an embodiment of the invention is illustrated in a commercially available state for use in the dental field, in which the bone substitute material K is shown filled in the cylinder. In the perspective illustration according to FIG. 1, the closure sleeve 7 is shown, surrounding the cylinder in a protective manner, and the end 20 of the cylinder 2 on the holding side, projecting therefrom, which otherwise rests, as already mentioned, in the closure sleeve 7. This end 20 of the cylinder 2 on the holding side comprises a grip plate 21. Reaching through out of the grip plate 21, the piston rod 3 includes a pressure plate 31 on the end side. The grip plate 21 is illustrated here as a separate part which is pressed in a form- and force-fitting manner onto the end 20 of the cylinder on the holding side. In an alternative embodiment, grip plate 21 can be produced integrally with the piston rod 3 as a semi-finished product, and on insertion or after insertion of the piston rod 3 can be separated with its piston 4 in place, and pressed onto the end 20 on the holding side. At this, of course, the predetermined breaking points between the grip plate 21 and the piston rod 3 are separated through. For the corresponding handling, the cylinder 2 has holding beads 22 at its end 20 on the holding side.

The cylinder 2 has an end 23 on the discharge side. This end 23 on the discharge side is provided with an external thread 24. An attachment 5 is screwed onto this external thread 24. Reference is to be made to the embodiment of the attachment 5 in connection with the description of FIGS. 6 to 10. In this embodiment, the attachment 5 forms a cover which ensures that the bone substitute material K, which is present in granulate form, cannot fall out. However, the attachment 5 has several openings in its cover surface and must therefore be sealed. In one embodiment, a closure sleeve 7 seals the openings in the attachment 5. With regard to the sealing, reference is to be made to the description of FIGS. 14 and 15. The closure sleeve 7 is secured on the one hand against rotations, and is also secured in the drawing-off direction by means of a form-fitting connection acting in axial direction. This takes place in the region of an upper ring 71 of the closure sleeve 7. In one embodiment, the closure sleeve 7 can, however, be separated from the remainder of the closure sleeve 7 by means of a warranty band 72, on which a tear-off lug 73 is formed.

Turning now to the embodiment of FIGS. 4 and 5, the closure sleeve 7 is now removed and the application device 1 is illustrated in a state after the bone substitute material has been pressed out. The cylinder 2 can be clearly seen, which has a widened inlet path 25 at the end 20 on the holding side. This widened inlet path 25 facilitates the assembly of the piston and cylinder. The grip plate 21 has a feedthrough opening 212. The end 20 of the cylinder 2 on the holding side engages into this feedthrough opening 212. In the region of the feedthrough opening 212, the grip plate 21 has a circumferential holding projection 211, directed towards the center. The circumferential holding projection 211 engages behind a retaining bead 213 which is sawtooth-shaped in cross-section and which is formed at the outermost end of the end 20 of the cylinder 2 on the holding side. In these two figures, the separated upper ring 71 can be seen, adhering to the end 20 of the cylinder on the holding side. It can also be seen here that the upper ring 71 has radially inwardly-directed teeth 74, which are held so as to be secured against rotation on the same such radially outwardly-directed teeth 214. The radially inwardly-directed teeth 74 on the upper ring 71 lie against a thickened retaining area 215. It is thereby ensured that the closure sleeve 7 in the warranty state cannot be removed without destroying the warranty band 72.

In one embodiment, a short external thread 26 can also be seen on the region of the widened inlet path 25 of the cylinder 2, but in the lower region, situated towards the end 23 on the discharge side. This external thread 26 serves to hold the closure sleeve 7 in a secured manner on the cylinder 2, and the closure sleeve 7 can then be unscrewed after removal of the warranty band.

At the end 23 on the discharge side, the thickness of the outer wall of the cylinder 2 is reduced and in this region 27 with reduced wall thickness, an external thread 28 is arranged. The region 27 with reduced wall thickness also runs flush with the external wall of the cylinder 2. The internal cross-section of the cylinder 2 does not alter from the widened inlet path 25 up to the lowermost end 23 on the discharge side. This consistent cross-section is due on the one hand to the piston 4, which of course does not alter its cross-section, and on the other hand it is thereby ensured that no blocking of the bone substitute material can take place during discharging.

At its lower end, which in the assembled state comes to lie in the direction of the end 23 on the discharge side, the piston rod 3 has a mushroom-shaped holding pin 30. In one embodiment, the holding pin is integrally formed with the piston rod. The mushroom-shaped holding pin 30 serves to fasten the piston 4. In one embodiment, the piston rod 3 is round in cross-section and corresponds approximately equally to the internal diameter of the cylinder 2. In another embodiment, to reduce material, the piston rod is configured from two plate-like elements disposed perpendicularly to each other, thus forming rod having a cross-shaped cross-section, which, however, of course may be manufactured as one part. In example shown, one of these plate-like elements forming the cross lies exactly in the sectional plane of the drawings.

As shown in FIG. 5, a discharge nozzle 6 can be screwed onto the cylinder 2. This discharge nozzle 6 is, in one embodiment, configured in a curved shape, so that thereby the bone substitute material which is to be discharged in the intended direction. For the dental applications of the lower jaw, normally the solution is used without the discharge nozzle 6, as shown by FIG. 4, whereas in the case of applications in the upper jaw, the discharge nozzle 6 will usually be used. If, however, the material is to be used in the mouth socket close to the pharyngeal space, then the curved shape discharge nozzle 6 may be utilized.

In FIGS. 6 to 10, the attachment 5 is now illustrated in detail. The attachment 5 resembles a screw cover. It has an outer wall 50 and an inwardly drawn cover surface 51. In order to increase the grip and hence to facilitate a screwing and unscrewing of the attachment 5, a number of axially running depressions 52 is formed on the external side of the outer wall 50. The cover surface 51 is drawn inwards in the inner region, so that on the internal side between the outer wall 50 and the inwardly drawn cover surface 51, an annular depression 53 remains. This annular depression 53 is configured such that the region 27 with reduced wall thickness finds a mounting therein in a sealing clamping manner. An internal thread 55 is formed in the region of the open end 54. This internal thread 55 is matched in a fitting manner to the external thread 28 on the region 27 with reduced wall thickness.

An injection opening 57 is formed centrally in the flat region 56 of the inwardly drawn cover surface 51. Several drainage openings 58 are grouped around the central injection opening 57. As the diameter of the injection opening and the diameter of the drainage opening are all of equal size, of course every drainage opening can also serve as an injection opening, just as the injection opening 57 can also serve as a drainage opening 58. Advantageously, the drainage openings 58 are arranged tangentially to the inwardly drawn, inclined cover surface portion 59. The practitioner can thereby use the inclined, inwardly-drawn cover surface portion 59 as a guide surface for the injection needle. This facilitates for him the introduction of the injection needle. It should be appreciated that the invention is not limited in this regard, and other suitably sized openings and/or arrangements may be employed.

The inwardly-drawn, inclined cover surface portion 59 also serves for sealing with the closure sleeve 7 which is to be placed over the cover surface, as will be described below.

Figure 12:
FIG. 12 shows the closure sleeve in perspective position.
Figure 13:
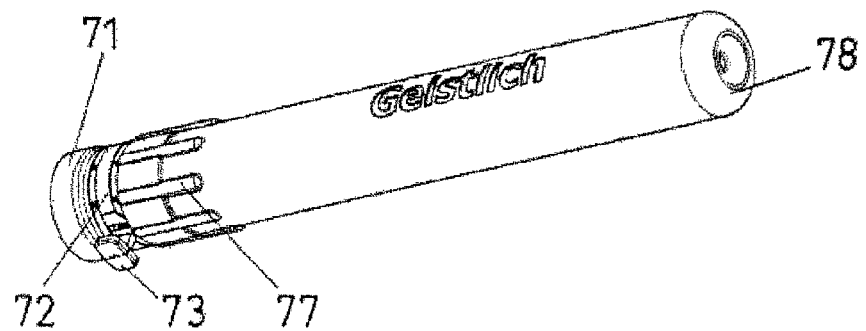
FIG. 13 illustrates the closure sleeve in perspective position rotated through 90'.

In FIGS. 11 to 13, the already mentioned closure sleeve 7 is illustrated by itself. The closure sleeve 7, according to one embodiment, has the shape of a tube with a closed end 75, opposite to the open end 76. As already described, the open end 76 has an upper ring 71. The warranty band 72, with its tear-off lug 73, follows in an adjoining manner in the direction of the closed end 75. In FIGS. 11 and 12, the annularly arranged region with the radially inwardly-directed teeth 74 can be clearly seen. Following from the warranty band 72 again in the direction of the closed end 75 is a region with externally arranged grip beads 77 running in axial direction.

In the closed end 75, which is formed by a base 78, an inwardly drawn sealing pin 79 is formed, directed towards the open end 76. This sealing pin 79 has a conical sealing wall 791 on the side lying externally in radial direction. In one embodiment, this conical sealing wall 791 fits exactly in a sealing manner into the inwardly drawn cover surface 51 of the attachment 5, as can be seen in FIG. 14. Hereby, a hermetic seal is achieved between the closure sleeve 7 and the attachment 5 in the mounted state. This is clearly illustrated in FIG. 14, wherein FIG. 14 reproduces the detail A of FIG. 2.

In FIG. 15, the detail B, as illustrated in FIG. 3, is shown on an enlarged scale. Here, the sealing surface 701 can be seen, which realizes a seal between the outer wall 70 of the closure sleeve 7 and the cylinder 2. This sealing surface 701 is situated beneath the internal thread on the region of the widened inlet path 25 in the direction of the discharge side. The sealing surface on the external side of the cylinder 2 is designated by 216 and can be seen in FIG. 5. These two sealing surfaces cooperate and increase the hermetic seal of the closure sleeve 7.

Figure 16:
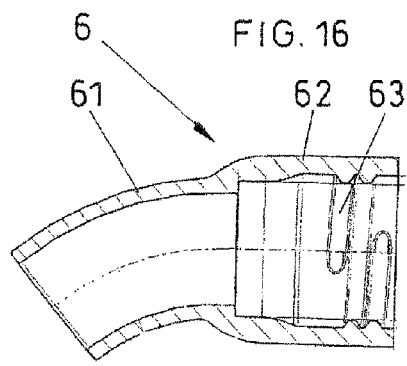
FIG. 16 shows a discharge nozzle in a diametral longitudinal section.
Figure 17:
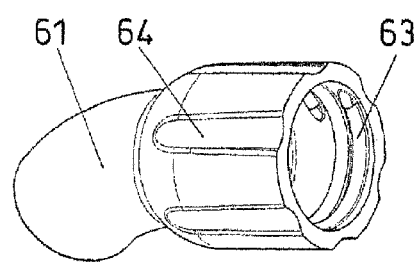
FIG. 17 shows the discharge nozzle in perspective representation.

In FIGS. 16 and 17, the discharge nozzle 6 is now illustrated in detail. The discharge nozzle 6 has a curved discharge tube 61, which is formed integrally on a screw bushing 62. The screw bushing has an internal thread 63, and in one embodiment, has on the external side, similar to the attachment 5, grip recesses 64. The internal diameter of the screw bushing 62 is greater than the internal diameter of the curved discharge tube 61. The increase in size is configured such that the region with reduced wall thickness 27 of the cylinder 2 fits in such a way that the internal outer wall surface of the cylinder 2 is exactly flush with the internal wall surface of the curved discharge tube. Therefore, the bone substitute material is not blocked upon discharge.

Figure 18:
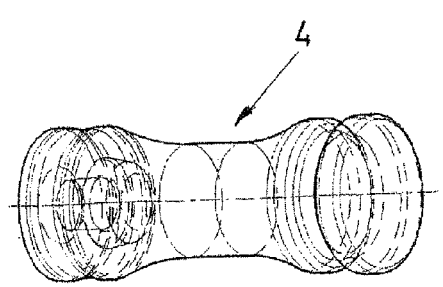
FIG. 18 shows a perspective representation of the flexible piston.
Figure 19:
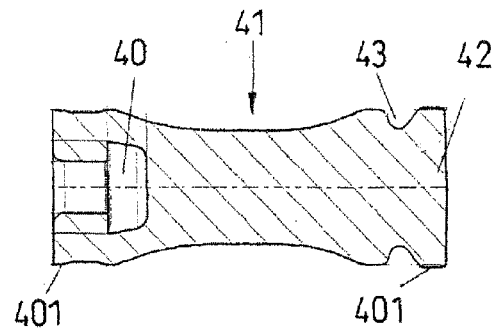
FIG. 19 shows the piston in a diametral longitudinal section.

In FIGS. 18 and 19, the piston 4 is illustrated in detail. In one embodiment, the piston 4 is made from an elastic material, for example from a silicone rubber. This piston 4, which as a whole is formed in one piece, has a mushroom-shaped mounting opening 40 at one end, in which the mushroom-shaped holding pin 30 on the piston rod 3 mounts in a form- and force-fitting manner. The outer wall of the piston is narrowed in the central region 41. On the discharge size, the piston 4 has a piston plate 42, which is followed by a displacement groove 43. The piston plate 42 has a slightly larger diameter than the following regions. An annular sealing surface 401 lies between the front side of the piston plate 42 and the displacement groove 43, and a same such sealing surface 401 is formed on the piston 4 in the direction of the end on the holding side. The narrowed region 41 between the two sealing surfaces 401 serves for the elastic piston 4 to be able to follow the curvature of the curved discharge tube 61 without jamming. Due to the pressure building up and the resistance on discharging the bone substitute material, the central, narrowed region is compressed and thereby conforms in diameter to the curved path of the discharge tube 61 largely in a sealing manner.

In one embodiment, the length of the piston 4 is at least approximately equal in length to the curved part of the discharge nozzle, namely the curved discharge tube 61. Advantageously, this piston is configured to be so long that the region in which the mushroom-shaped holding pin 30 projects into the mushroom-shaped mounting opening 40 still lies inside the region of the cylinder, and only the portion of the elastic piston 4 lying in front thereof lies inside the curved discharge tube of the discharge nozzle 6. In fact, the elastic piston 4 can also be longer, but in any case not shorter than the curved discharge tube, because otherwise the piston rod 3, which is not flexible, would project into the discharge nozzle and would tilt or jam.

Thus, in one embodiment, a total emptying of the device may be achieved.

It should be understood that although a mushroom-shaped opening and pin is shown and described, the invention is not limited in this regard and other suitable cooperating shapes may be utilized.

Figure 20:
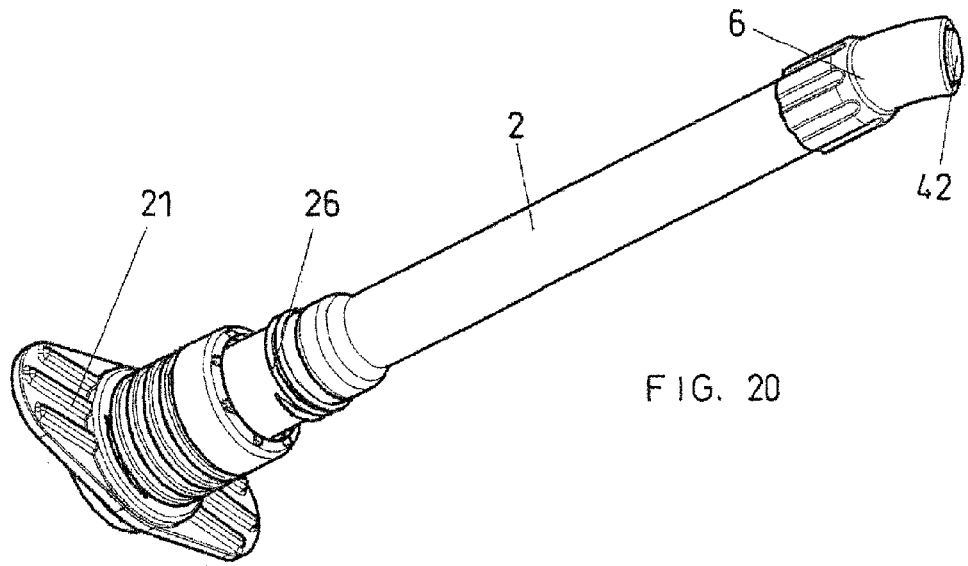
FIG. 20 shows the device according to an embodiment of the invention after the first use with a curved discharge nozzle, placed in position, in the completely emptied state.

In FIG. 20, the situation is now illustrated as in FIG. 5 again in perspective position. It can be seen that the piston plate 42 now projects slightly over the terminal edge of the curved discharge tube 61. It is thereby ensured that the already placed bone substitute material can also be completely discharged and used.

A new method is produced due to the device according to an embodiment of the invention. With this new method, the bone substitute material lies in granular consistency in a cylinder of an application syringe, stored in a sealed manner. The application syringe is closed off with an attachment 5. This attachment has at least one injection opening and several drainage openings. In a first step, by means of an injection syringe, swelling fluid is injected through the injection opening in the attachment into the granular bone substitute material. During a certain action time, the bone substitute material now swells up. In a second step, the swollen material is now pressed. This takes place in the device according to an embodiment of the invention by pressure being applied onto the pressure plate 31 of the piston rod 3. Here, the excess swelling fluid is ejected through the drainage openings and partially also through the injection opening, which now free again, and consequently the swollen material is compacted. The attachment 5 is now removed and thereafter the compacted, swollen material can be pressed out in the form of a rope. If applicable, the unscrewed attachment 5 is replaced by a curved discharge nozzle 6.

One proceeds as follows with the device according to an embodiment of the invention. Firstly, one grasps the tear-off lug 73 and by means thereof one tears off the warranty band 72. Hereby, the closure sleeve 7 separates itself from the upper ring 71, which now remains at the end on the holding side in the region of the widened inlet path 25. One now grasps the closure sleeve 7 and unscrews the latter from the external thread 26 of the widened inlet path. As both the drainage openings and also the injection opening 57, 58 are smaller in diameter than the grain size of the granulate, the latter does not emerge from the cylinder 2. By means of an injection syringe, which is available in every medical practice, the liquid phase is now injected in the space in which the granulate is present. That liquid phase may be e.g. the patient's own blood or a physiological saline solution. After a certain time, which can be seen from the enclosure in the packaging, the practitioner will grasp the device, with the index finger and middle finger usually lying against the grip plate and the thumb acting on the pressure plate. Hereby, the piston 4 is pushed forward and the excess liquid phase is ejected through the openings 57, 58. Depending on the pressure which is applied, the practitioner increases the desired consistency for his application. Thereafter, the practitioner removes the attachment 5, which therefore serves initially as a sealing cap during storage and has now served as a sieve plate for drainage. If the practitioner now applies pressure again onto the pressure plate 31, then the desired amount of the bone substitute material (up to the total amount present in the device) in the desired consistency can be ejected.

In contrast to known embodiments, the practitioner obtains here, for the first time, a device by means of which he can himself determine the consistency of the bone substitute material and this is not determined solely through the corresponding predetermined quantities of the mixture which is to be prepared.

Having thus described several aspects of at least one embodiment of this invention, it is to be appreciated various alterations, modifications, and improvements will readily occur to those skilled in the art. Such alterations, modification, and improvements are intended to be part of this disclosure, and are intended to be within the spirit and scope of the invention. Accordingly, the foregoing description and drawings are by way of example only.

What is claimed is:

1. A device for the application of bone substitute material comprising:
   a cylinder, in which the bone substitute material is situated in granular consistency, with an end on the holding side and an end on the discharge side, the end of the cylinder on the discharge side is provided with an external thread, on which a removable attachment with an internal thread and adapted to close the cylinder is held;
   a piston rod situated in the cylinder, on which piston rod a sealing piston is placed;
   a curved discharge nozzle which can replace the attachment and be held on the end of the cylinder on the discharge side provided with the external thread, wherein the sealing piston is a single-piece, rubber-elastic and flexible element, the length of which corresponds at least approximately to the length of the curved discharge nozzle; and
   an injection opening in the removable attachment for injecting fluid into the cylinder where the granular bone substitute material is situated and with several drainage openings arranged around the injection opening.

2. The device according to claim 1, wherein the piston rod is embodied so as to be resistant to bending.

3. The device according to claim 1, wherein the piston rod is provided with radially outwardly-directed reinforcing ribs.

4. The device according to claim 1, wherein the removable attachment has an annular depression, embracing the cylinder wall in a sealing manner.

5. The device according to claim 1 wherein the removable attachment has a cover surface which is placed downwards with respect to an outer, encircling edge, so that in the state when in position, the cover surface with the injection opening and the drainage openings lies inside the interior of the cylinder.

6. The device according to claim 5, wherein the cover surface is embodied conically from the region of the outer, encircling edge to the downwardly placed, flat part of the cover surface.

7. The device according to claim 1, wherein the discharge nozzle has an internal diameter which corresponds exactly to the internal diameter of the cylinder.

8. The device according to claim 1, wherein the rubber-elastic piston has an annular sealing surface on both ends, and the region between the two sealing surfaces continuously narrows in diameter and becomes thicker again.

9. The device according to claim 1, wherein the discharge nozzle has a discharge opening and also an inlet opening, wherein these two openings form an angle between 20° and 70°.

10. The device according to claim 1, wherein the device further comprises a sealing closure sleeve closed on one side and having an internal thread, wherein the end of the cylinder on the holding side is thickened in wall thickness and is provided with an external thread, on which the sealing closure sleeve can be screwed.

11. The device according to claim 10, wherein the closure sleeve has on the closed end an inwardly-directed, conical sealing pin, which in the mounted state before a first use of the device, engages in a sealing manner in the conical region of the cover surface of the removable attachment.

12. A device according to claim 10, wherein the closure sleeve, before a first use of the device, is connected with the cylinder via a warranty band.

* * * * *

UNITED STATES PATENT AND TRADEMARK OFFICE
CERTIFICATE OF CORRECTION

PATENT NO.        : 8,491,592 B2  
APPLICATION NO.   : 13/250383  
DATED             : July 23, 2013  
INVENTOR(S)       : Werner F. Dubach It is certified that error appears in the above-identified patent and that said Letters Patent is hereby corrected as shown below:

On the Title page, in item (30), replace "10185348" with --10185348.9--

Item (30) should read: Oct. 1, 2010   (EP) ..................................... 10185348.9

Signed and Sealed this  
Twenty-fourth Day of September, 2013

Teresa Stanek Rea  
*Deputy Director of the United States Patent and Trademark Office*